(12) United States Patent
Nie et al.

(10) Patent No.: US 8,019,431 B2
(45) Date of Patent: Sep. 13, 2011

(54) ENHANCED SIGNAL PROCESSING FOR COCHLEAR IMPLANTS

(75) Inventors: Kaibao Nie, Bothell, WA (US); Les Atlas, Seattle, WA (US); Jay Rubinstein, Seattle, WA (US); Xing Li, Bellevue, WA (US); Charles Pascal Clark, Seattle, WA (US)

(73) Assignee: University of Washington, Seattle, WA (US)

( * ) Notice: Subject to any disclaimer, the term of this patent is extended or adjusted under 35 U.S.C. 154(b) by 204 days.

(21) Appl. No.: 12/476,979

(22) Filed: Jun. 2, 2009

(65) Prior Publication Data

US 2009/0312820 A1     Dec. 17, 2009

Related U.S. Application Data

(60) Provisional application No. 61/057,994, filed on Jun. 2, 2008.

(51) Int. Cl.
*A61N 1/00* (2006.01)
(52) U.S. Cl. .......................................................... 607/57
(58) Field of Classification Search .................... 607/57; 600/25
See application file for complete search history.

(56) References Cited

U.S. PATENT DOCUMENTS

| | | | |
|---|---|---|---|
| 5,772,575 A | 6/1998 | Lesinski et al. | 600/25 |
| 5,881,158 A | 3/1999 | Lesinski et al. | 381/174 |
| 5,951,601 A | 9/1999 | Lesinski et al. | 623/10 |
| 5,977,689 A | 11/1999 | Neukermans | 310/324 |
| 6,068,589 A | 5/2000 | Neukermans | 600/25 |
| 6,153,966 A | 11/2000 | Neukermans | 310/328 |
| 6,381,336 B1 | 4/2002 | Lesinski et al. | 381/326 |
| 6,565,503 B2 | 5/2003 | Leysieffer et al. | 600/25 |
| 6,611,718 B2 | 8/2003 | Zilberman et al. | 607/57 |
| 2003/0055311 A1 | 3/2003 | Neukermans et al. | 600/25 |
| 2009/0226016 A1* | 9/2009 | Fitz et al. | 381/316 |

FOREIGN PATENT DOCUMENTS

| | | |
|---|---|---|
| WO | WO 97/30565 | 8/1997 |
| WO | WO 97/44987 | 11/1997 |
| WO | WO 03/037212 | 5/2003 |

OTHER PUBLICATIONS

"Coherent Envelope Detection . . . " Steven Schimmel and Les Atlas, 0-7803-8874-7/05 IEEE; ICASSP 2005, pp. 1-221 to 1-224.*
"Coherent Envelope Detection . . . " by Steven Schimmel and Les Atlas, 0-7803-8874-7/05 IEEE: ICASSP 2005, pp. 1-221 to 1-224.*
Loizou, Philipos C., "Introduction to cochlear implants." IEEE Signal Processing Magazine; 64pp, Sep. 1998. <http://www.utdallas.edu/~loizou/cimplants/tutorial/tutorial.htm>.

* cited by examiner

*Primary Examiner* — George Manuel
*Assistant Examiner* — Robert Wieland

(57) ABSTRACT

The restoration of melody perception is a key remaining challenge in cochlear implants. A novel sound coding strategy is proposed that converts an input audio signal into time-varying electrically stimulating pulse trains. A sound is first split into several frequency sub-bands with a fixed filter bank or a dynamic filter bank tracking harmonics in sounds. Each sub-band signal is coherently downward shifted to a low-frequency base band. These resulting coherent envelope signals have Hermitian symmetric frequency spectrums and are thus real-valued. A peak detector or high-rate sampler of half-wave rectified coherent envelope signals in each sub-band further converts the coherent envelopes into rate-varying, interleaved pulse trains. Acoustic simulations of cochlear implants using this new technique with normal hearing listeners, showed significant improvement in melody recognition over the most common conventional stimulation approach used in cochlear implants.

24 Claims, 13 Drawing Sheets

Two melody notes: a subband signal (A), its Hilbert envelope (B), and the real coherent envelope (C).

CIS ENCODING (PRIOR ART)

ENHANCED SIGNAL PROCESSING FOR COCHLEAR IMPLANTS

RELATED APPLICATIONS

This application is based on provisional application Ser. No. 61/057,994, filed on Jun. 2, 2008, the benefit of the filing date of which is hereby claimed under 35 U.S.C. §119(e).

GOVERNMENT RIGHTS

This invention was made with government support under grant numbers FA 9550-06-1-0191 and FA 9550-09-1-0060 awarded by the Air Force Office of Scientific Research, and grant numbers R01 DC007525 and P30 DC 004661 awarded by the National Institutes of Health. The government has certain rights in the invention.

BACKGROUND

More than 100,000 patients worldwide with profound hearing loss have received cochlear implants as a clinical treatment to regain partial hearing. In current cochlear implants, most speech coding strategies extract and deliver a small number of temporal envelope cues via pulsatile electrical stimulation.

Unfortunately, cochlear implants are limited in that the patient can only perceive relatively low frequency signals induced by the cochlear implant. Natural speech and music include both relatively high frequency and relatively low frequency components, and existing cochlear implant signal processing techniques do not extract useful information from the relatively high frequency portions of acoustical inputs. As a result, cochlear implants have relatively poor performance in noisy environments and in regard to the perception of music.

In the widely used continuous interleaved sampling (CIS) coding scheme, sounds are split into a few sub-bands, and the slowly varying envelopes are extracted with a half-wave or full-wave rectifier followed by a low-pass filter in each sub-band. This technique provides a signal that can be used to successfully control cochlear implants to enable users to perceive speech in relatively quiet environments. However, the CIS encoding scheme does not extract much useful information from the relatively high frequency portions of acoustical inputs. Other prior art signal processing techniques for cochlear implants have calculated envelopes from the magnitude of the Fast Fourier Transform (FFT) or the Hilbert transform. Again, such techniques do not extract much useful information from the relatively high frequency portions of acoustical inputs.

This issue can be better understood by examining the following sum-of-product model for any given sound signal x(t), as shown in Eq. (1):

$$x(t) = \sum_{k=1}^{N} x_k(t) = \sum_{k=1}^{N} a_k(t) \cdot c_k(k) \tag{1}$$

where k is a sub-band index, $x_k(t)$ is the output for each of N sub-bands, $a_k(t)$ is a slowly varying envelope, and $c_k(t)$ is a higher-frequency carrier. Some type of detection rule is used to determine the product decomposition of each sub-band output ($x_k(t) = a_k(t) \cdot c_k(t)$) into slowly varying amplitude and higher frequency carrier signals, respectively.

The envelope signal $a_k(t)$ can be derived from the amplitude of Fourier transform, or by incoherent demodulations, e.g., half-wave rectification, full-wave rectification, and the Hilbert transform. In current cochlear implants, only the positive envelope signal $a_k(t)$ is coded in each sub-band, resulting in significant loss of information contained in the carrier signal or temporal fine structure $c_k(t)$.

For example, a detection rule used in existing cochlear implants decomposes each sub-band signal $x_k(t)$ into a Hilbert envelope and an associated carrier. This approach begins with the determination of the analytic signal as shown in Eq. (2):

$$\tilde{x}_k(t) = x_k(t) + jH\{x_k(t)\} \tag{2}$$

where $H\{x_k(t)\}$ is the Hilbert transform of $x_k(t)$. The amplitude portion of the signal is non-negative and the real magnitude of the analytic signal is as shown in Eq. (3):

$$a_k(t) = |\tilde{x}_k(t)|. \tag{3}$$

The result from Eq. (3) is commonly referred to as the "Hilbert envelope." The carrier portion of the signal is the remaining uni-modular phase of the analytic signal, as shown in Eq. (4):

$$c_k(t) = \cos\left\{\tan^{-1}\frac{\operatorname{Im}\tilde{x}_k(t)}{\operatorname{Re}\tilde{x}_k(t)}\right\} = \cos\varphi_k(t). \tag{4}$$

Thus, in current cochlear implants, only the non-negative and real envelope $a_k(t)$ is delivered to the selected stimulating electrode at a fixed stimulation rate. The conventional envelope extraction process eliminates the temporal fine structure cues (cos $\phi_k(t)$) in each sub-band, yielding a coarse spectral and temporal representation of speech and music sounds. Psychoacoustic experiments have shown that, with a limited number of envelopes, most patients are still able to understand speech relatively well and they can even converse over the phone. However, among the majority of cochlear implant users, the lack of temporal fine structure has led to poor speech recognition in noisy environments, near-chance level of melody recognition, poor Mandarin tone recognition and production, and inability to use ITD (Inter-aural Timing Difference) cues to localize sounds.

The encoding of temporal fine structure in cochlear implants is ultimately restricted by the ability of temporal pitch perception in electrical stimulation. Studies have shown that cochlear implant patients can only perceive stimulated rate variations up to about 1000 Hz. However, the frequency content of the temporal fine structure (cos $\phi_k(t)$) in speech and music can be up to 10,000 Hz at higher spectral sub-bands and it is not a band-limited signal.

It would therefore be desirable to provide an acoustical signal processing technique that extracts useful information from the frequency content of the temporal fine structure, to provide enhanced implant performance to users of cochlear implants.

SUMMARY

This application specifically incorporates by reference the disclosures and drawings of each patent application and issued patent identified above as a related application.

As noted in the discussion above, cochlear implant patients can only perceive stimulated rate variations up to about 1000 Hz, while the frequency content of the temporal fine structure (cos $\phi_k(t)$) in speech and music can be up to 10,000 Hz at higher spectral sub-bands. In broad terms, the concepts disclosed herein can be used to extract useful information from relatively high frequency portions of an acoustic input (i.e., the temporal fine structure), and to convert that information into a relatively low frequency, slowly varying signal that is compatible with cochlear implants, to provide enhanced implant performance for users of cochlear implants. In a particularly exemplary, but not limiting embodiment, the enhanced signal processing disclosed herein can be used with existing cochlear implant hardware.

In more detailed terms, one aspect of the concepts disclosed herein uses a single sideband demodulation approach to coherently shift a sub-band signal to its base band, generating a low-frequency, real coherent envelope signal. Such a signal will encode both temporal envelope and fine structure cues in a slowly varying manner that is compatible with the frequency limitations of cochlear implant technology. This sideband demodulation makes it feasible to deliver perceivable temporal cues originating in the temporal fine structure of higher frequency portions of the original audio spectrum.

One aspect of the concepts disclosed herein is directed to a method for controlling a cochlear implant for a hearing impaired patient. An exemplary method includes the steps of providing an auditory input signal, determining a pitch of the auditory input signal over time, and separating the auditory input signal into a plurality of harmonics over time as a function of the pitch over time. For each of the plurality of harmonics, the frequency of the harmonic is shifted downward, generating a plurality of frequency shifted harmonics. For each of the frequency shifted harmonics, an amplitude modulation is performed, generating a plurality of frequency shifted and amplitude modified harmonics, and each frequency shifted and amplitude modified harmonic is mapped to at least one of a plurality of cochlear implant stimulation electrodes.

Another aspect of the concepts disclosed herein is directed to the use of coherent envelope separation in signal processing for cochlear implants. Prior art signal processing for cochlear implants (such as the CIS encoding and Hilbert envelope encoding discussed above) employ non-coherent envelope separation. A novel coherent envelope separation technique for cochlear implants using a time-varying carrier estimate chosen as a center of sub-band gravity is disclosed herein. The resulting coherent envelope is a complex quantity, which is not suitable to be coded in electrical stimulation. Additional processing is required to enable the extracted information from the temporal fine detail to be included in a relatively low frequency, slowly varying signal that is compatible with cochlear implants. To achieve such a relatively low frequency, slowly varying signal, it is assumed that the carrier $w_k(t)$ is fixed at the lower boundary of each sub-band. Such a coherent envelope extraction approach has minimal information loss, and the corresponding coherent envelope is a real-valued signal as a result of direct spectral shifting.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1 is a flow chart of exemplary high level method steps for using coherent demodulation in an enhanced signal processing paradigm for use with cochlear implants, which provides enhanced cochlear implant performance by extracting useful information from relatively high frequency portions of an acoustic input (i.e., the temporal fine structure) and including that information in a relatively low frequency, slowly varying signal compatible with cochlear implants;

Figure 2A:
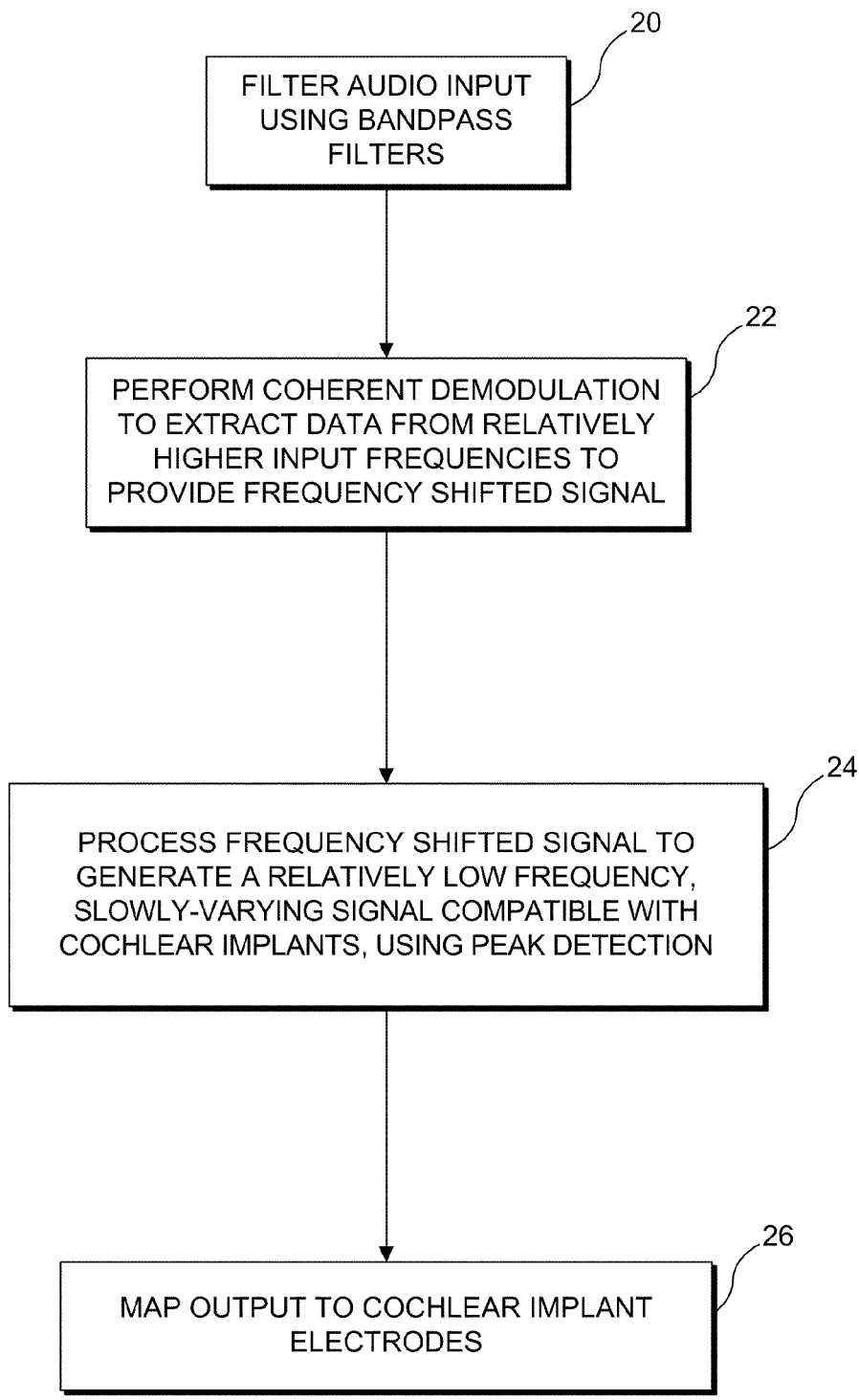
FIG. 2A is a flow chart of exemplary method steps in a first exemplary technique disclosed herein for using coherent demodulation in an enhanced signal processing paradigm for use with cochlear implants, which employs bandpass filtering.
Figure 2B:
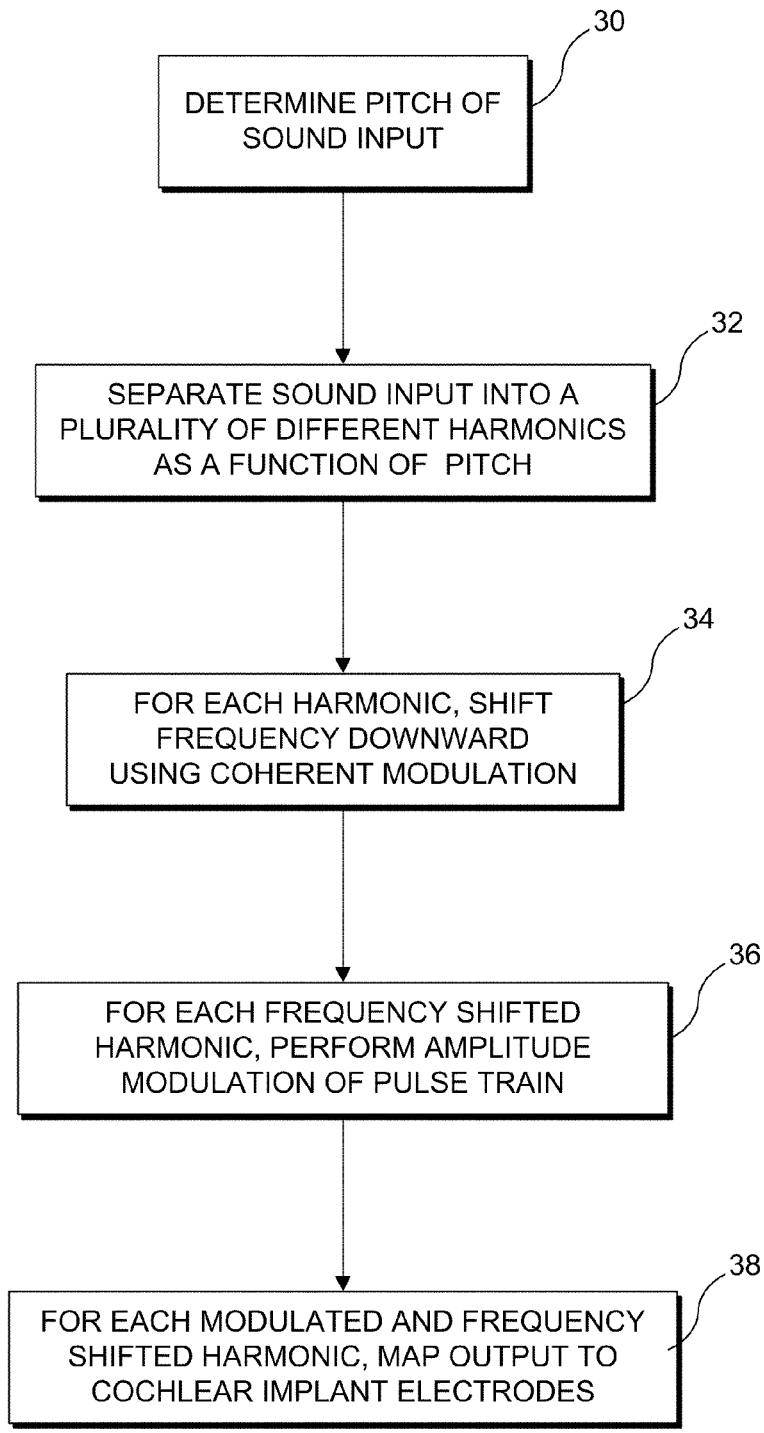
FIG. 2B is a flow chart of exemplary method steps of a second technique, for using coherent demodulation in an enhanced signal processing paradigm that employs harmonic filtering and is usable with cochlear implants.
Figure 3:
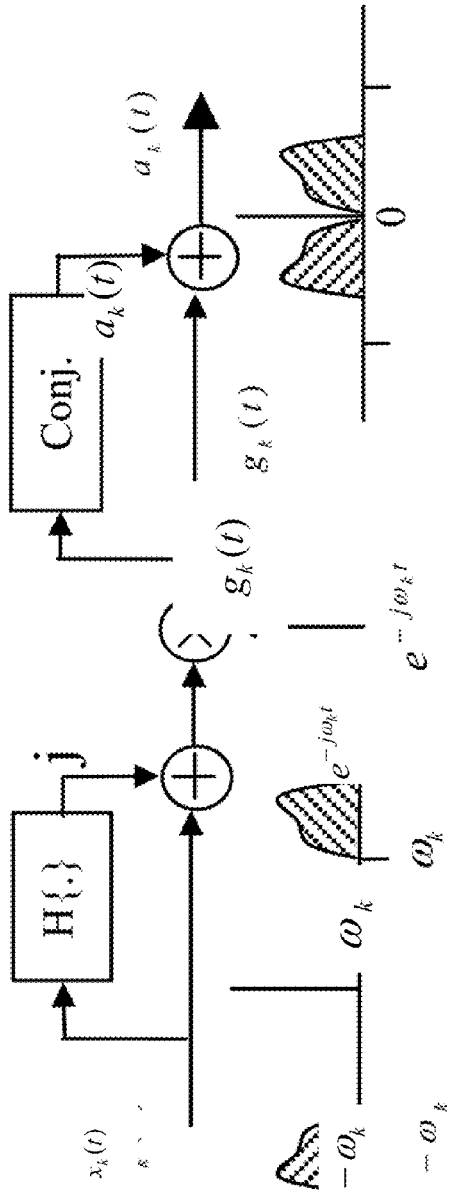
Figure 6:
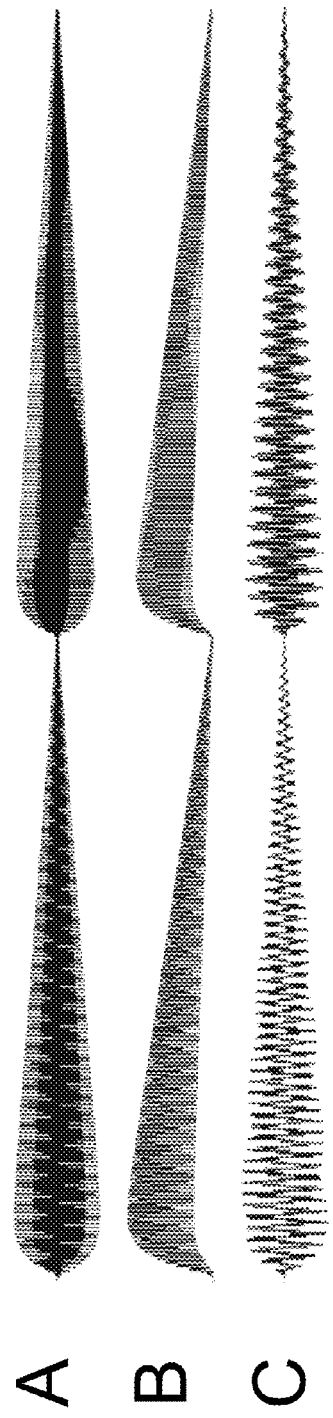
Figure 4A:
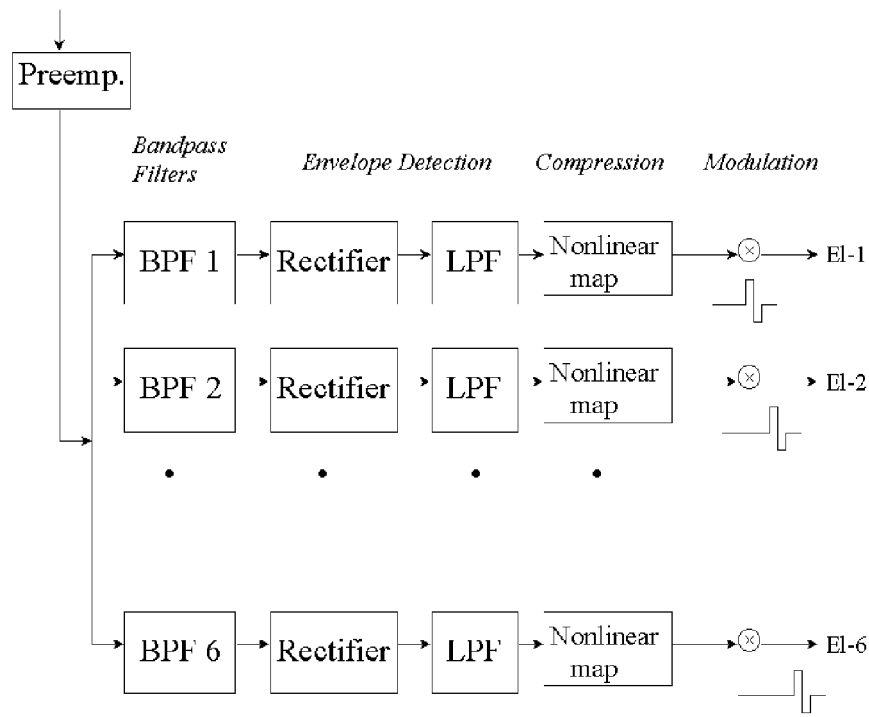
Figure 4B:
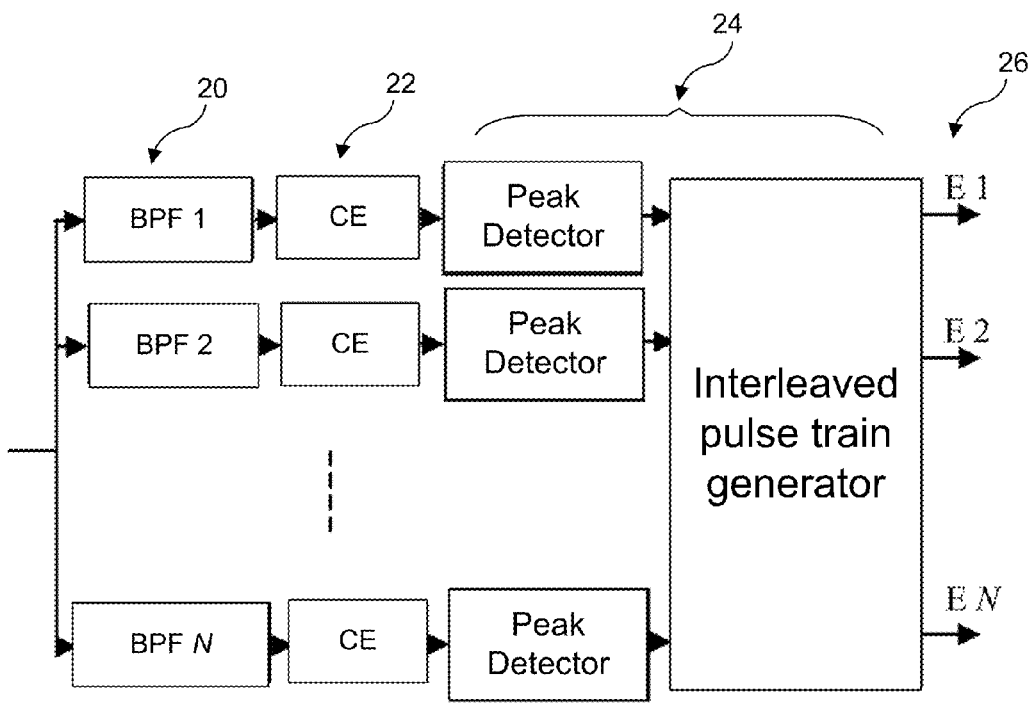
Figure 5A:
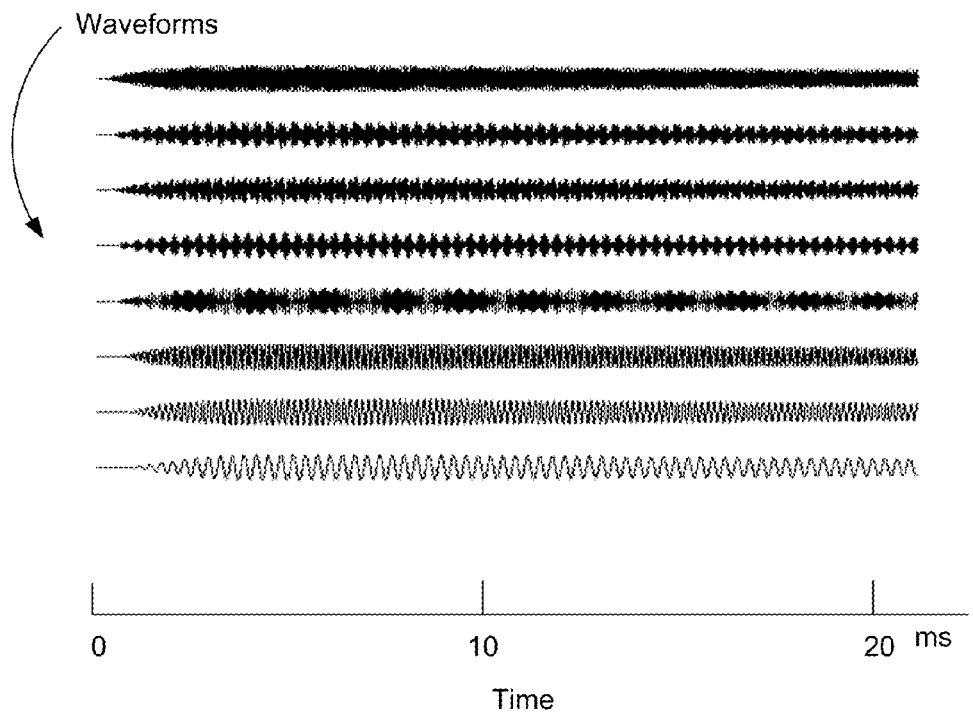
Figure 5B:
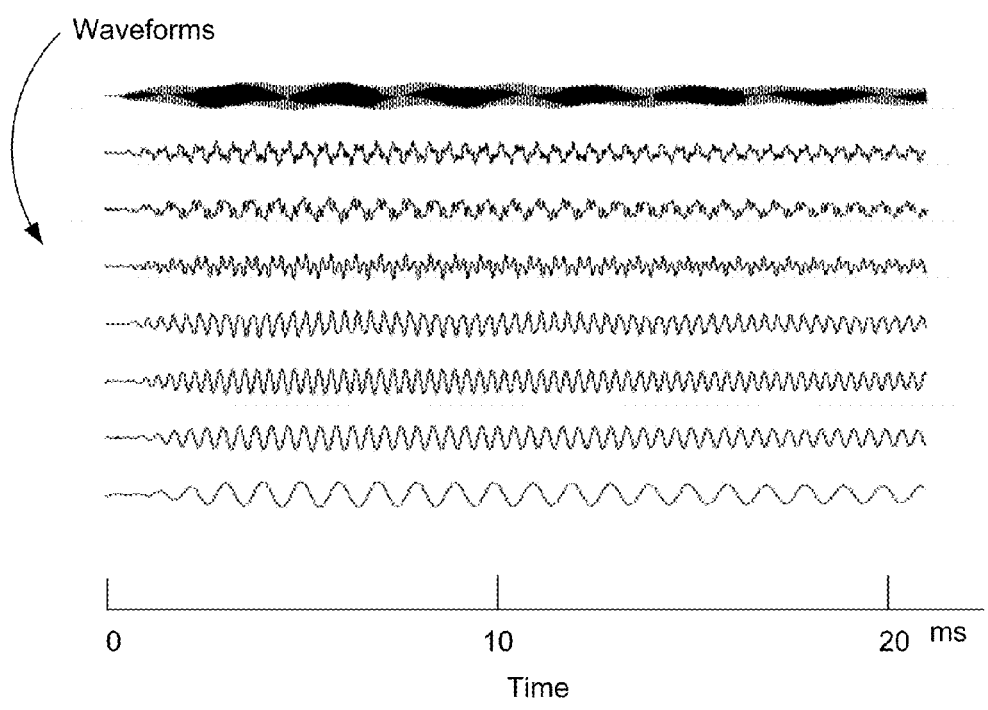
Figure 7A:
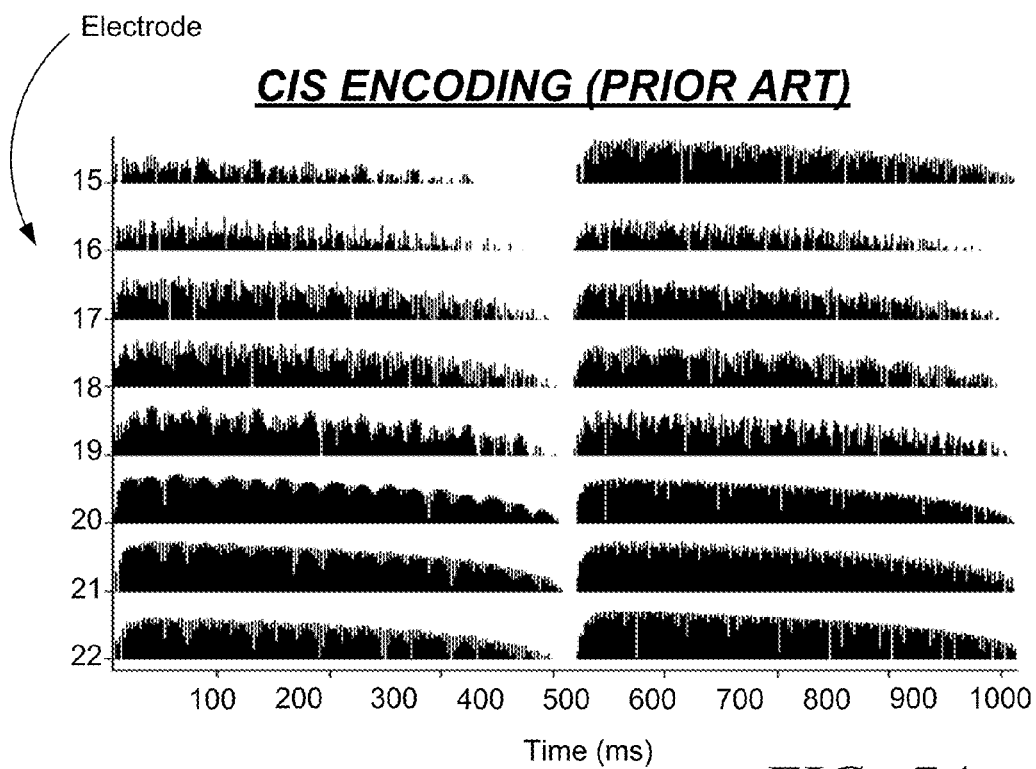
Figure 7B:
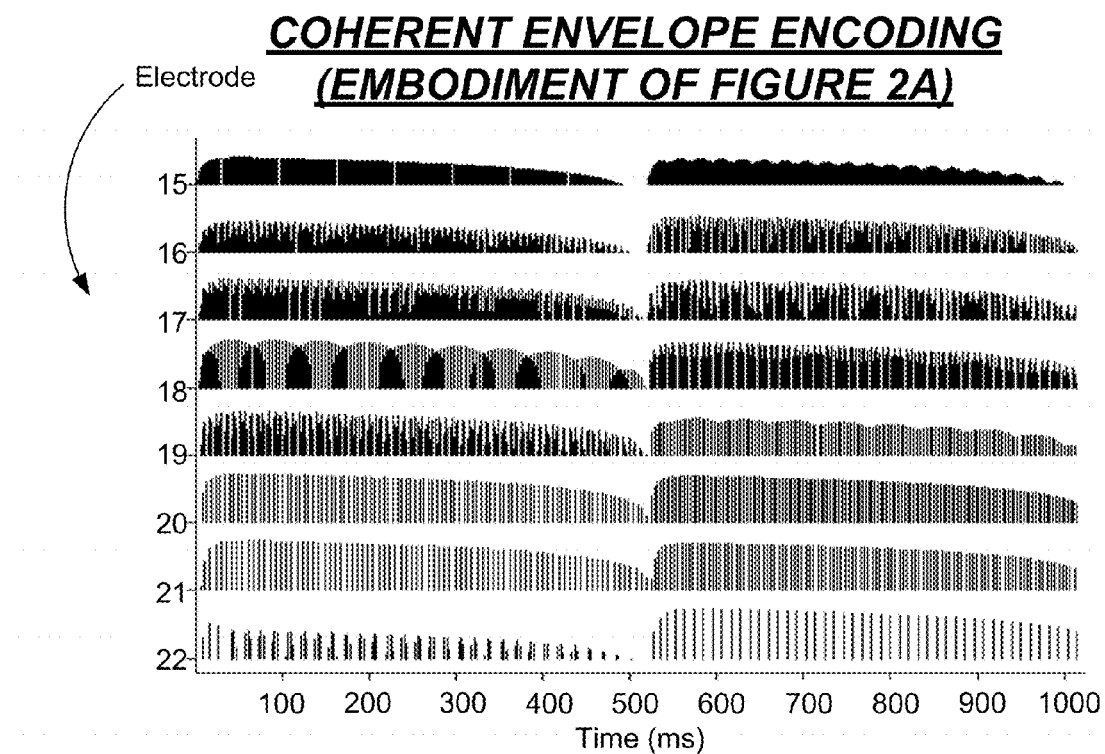
Figure 7C:
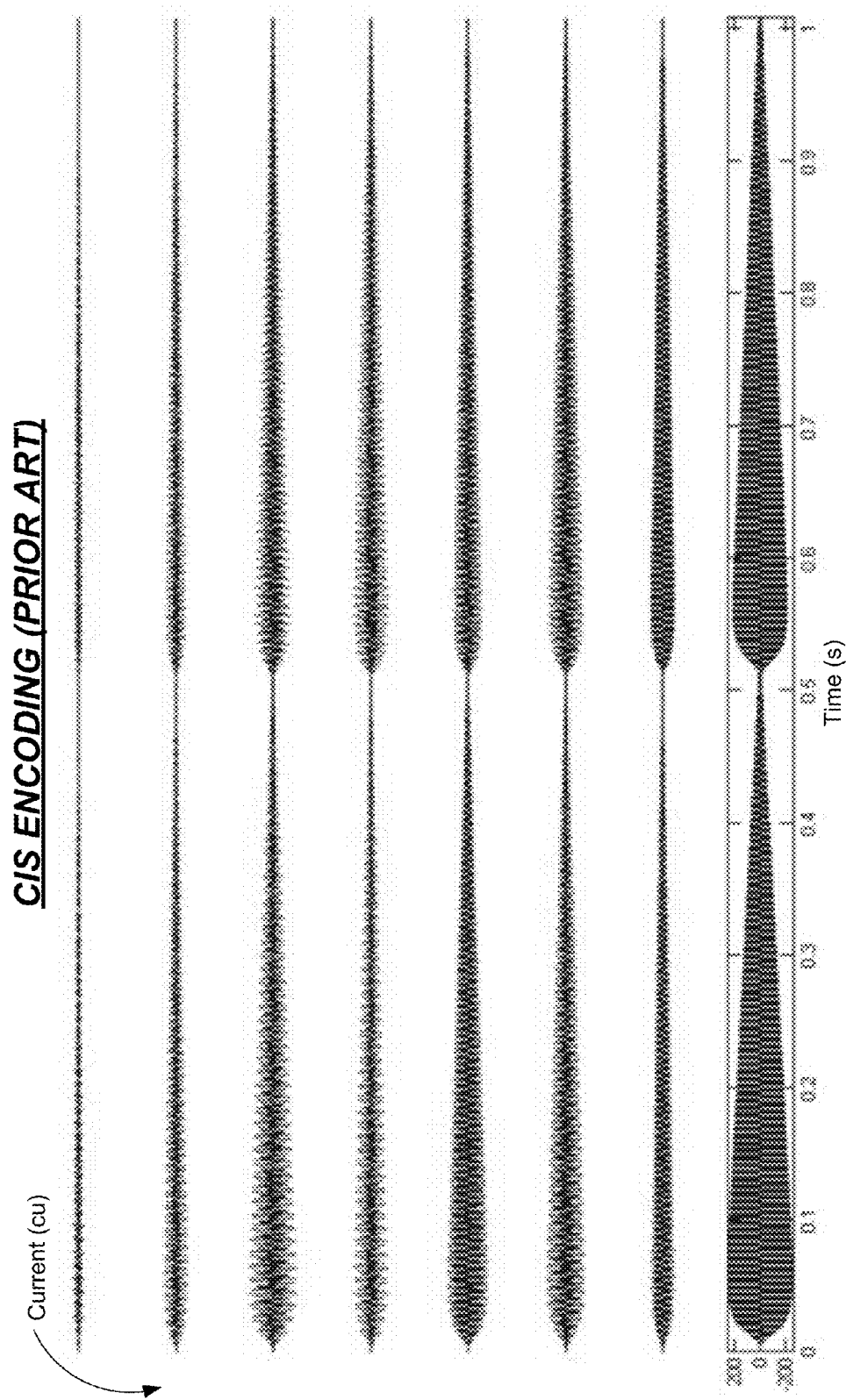
Figure 7D:
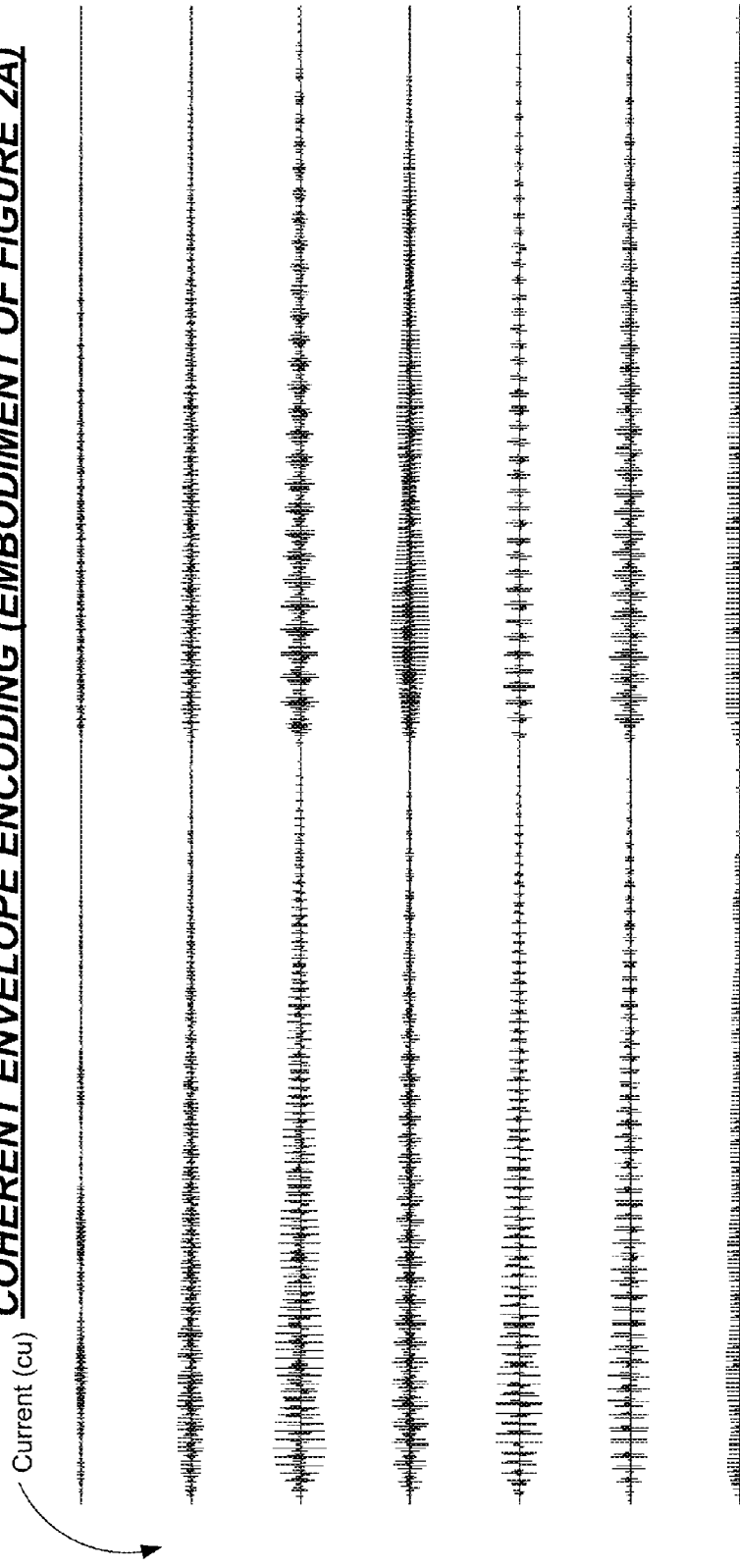
Figure 8:
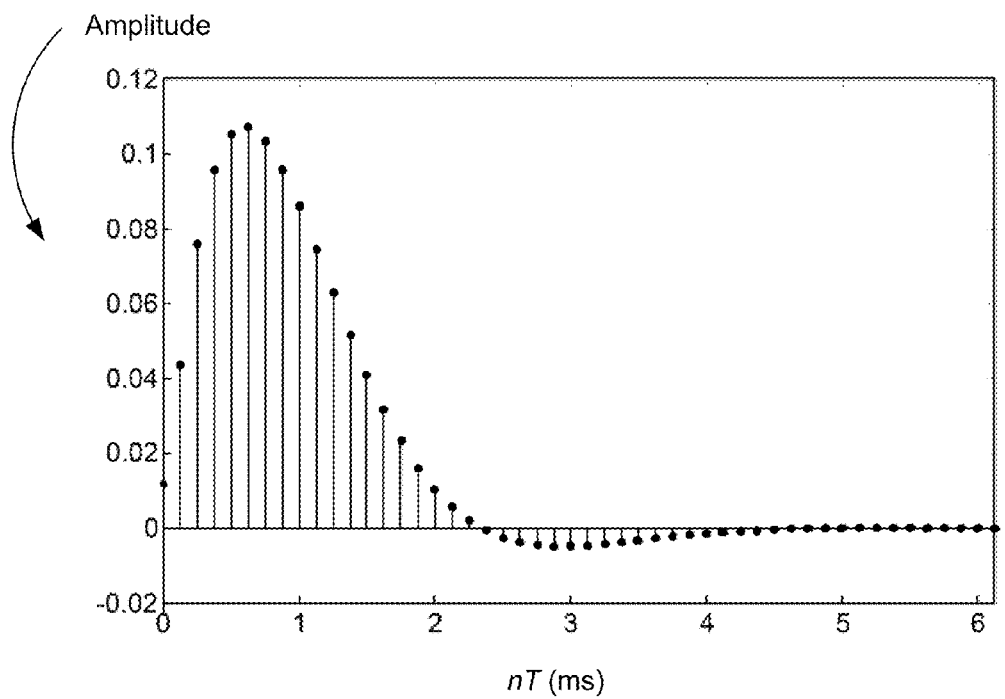
Figure 9:
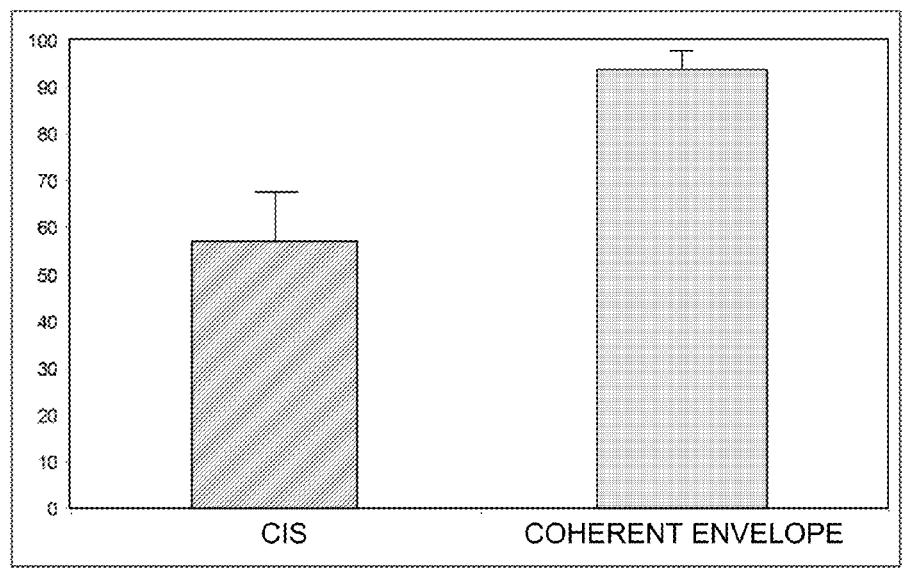
Figure 10:
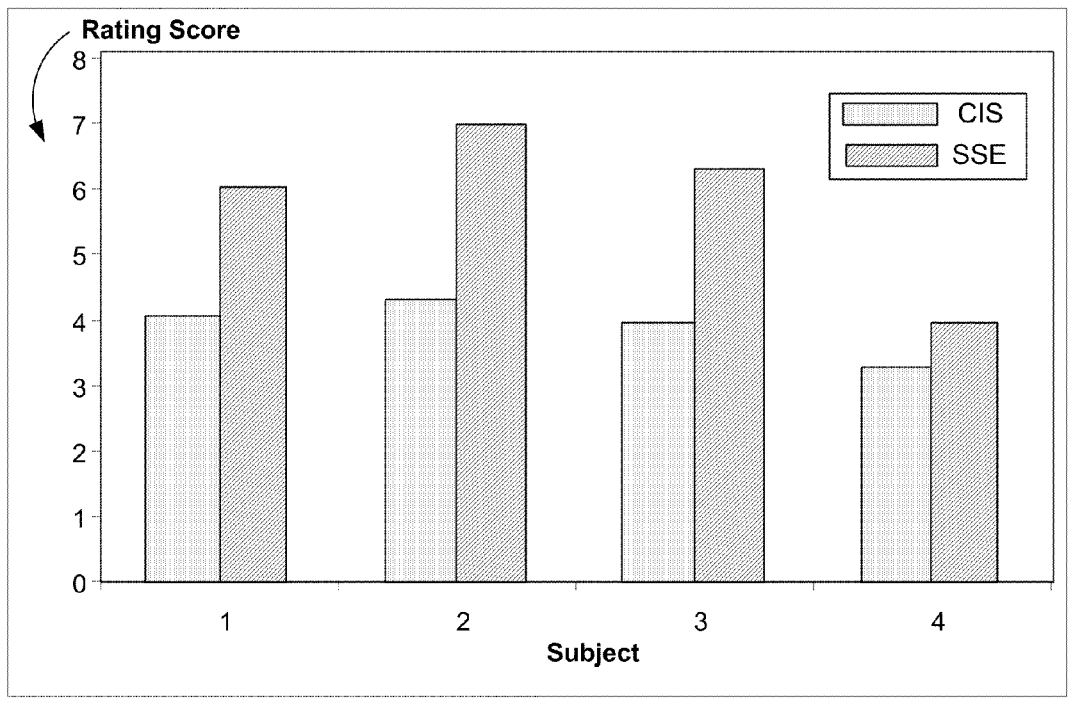
Figure 11:
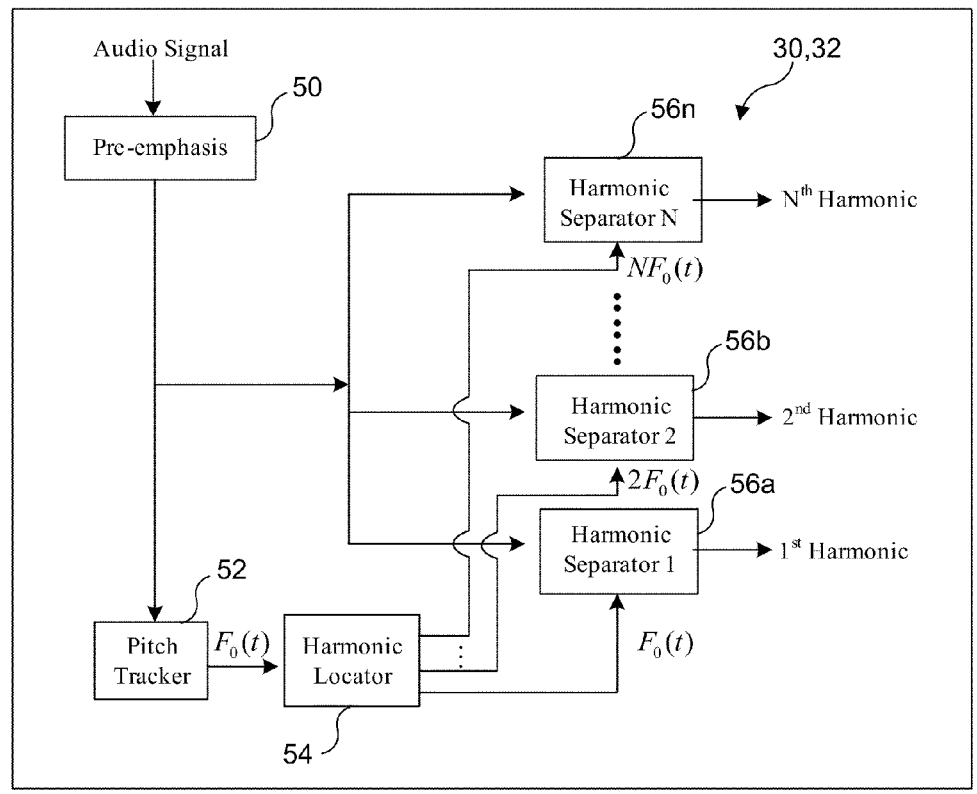
Figure 12:
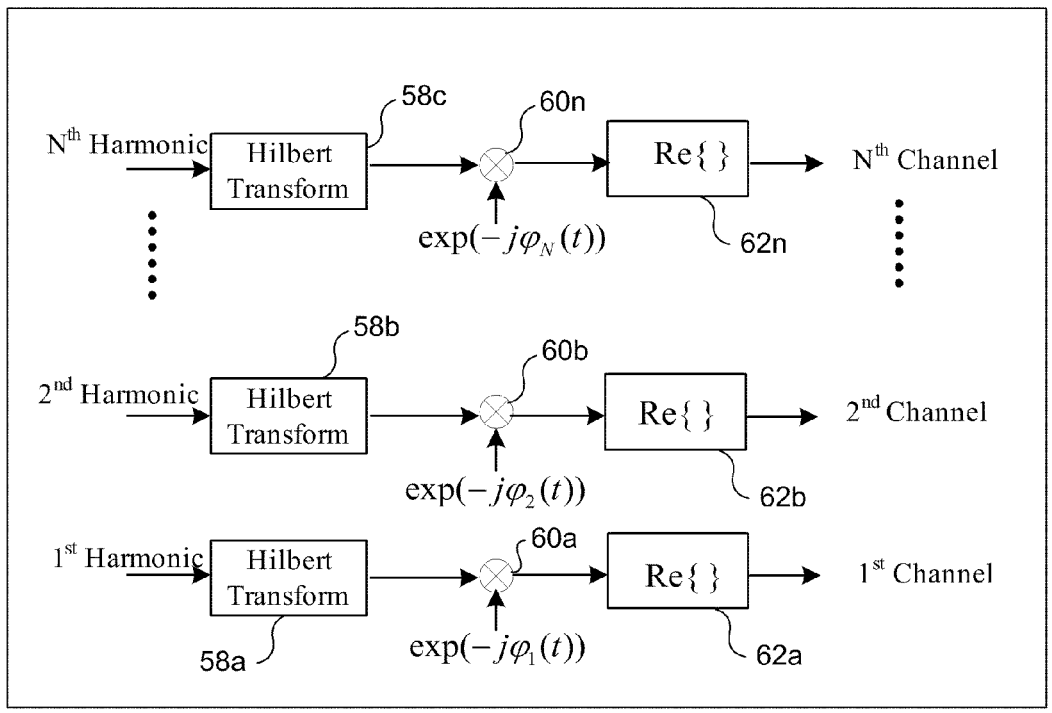
Figure 13:
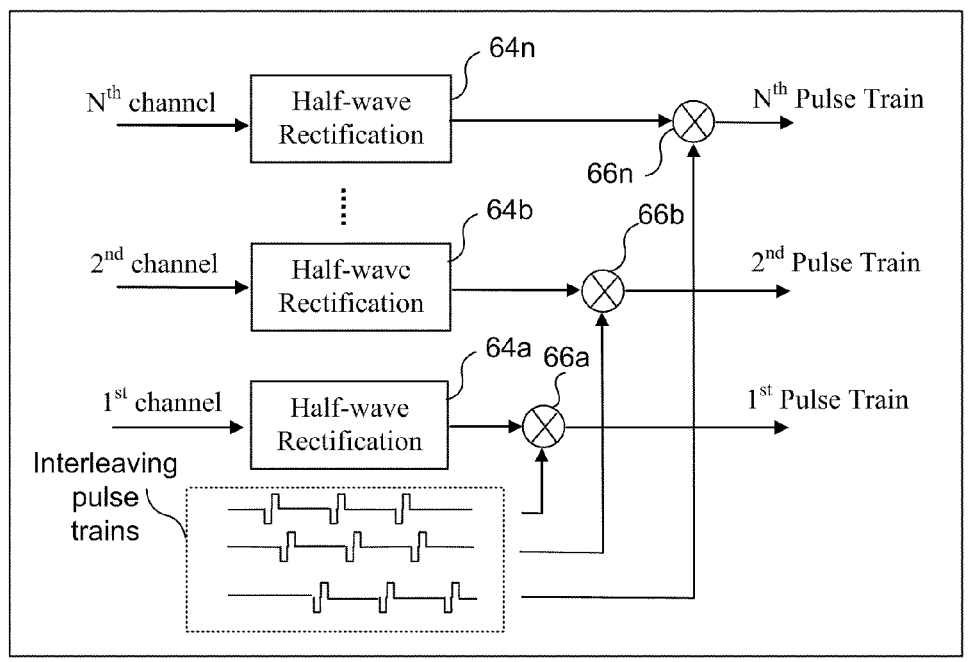
Figure 14:
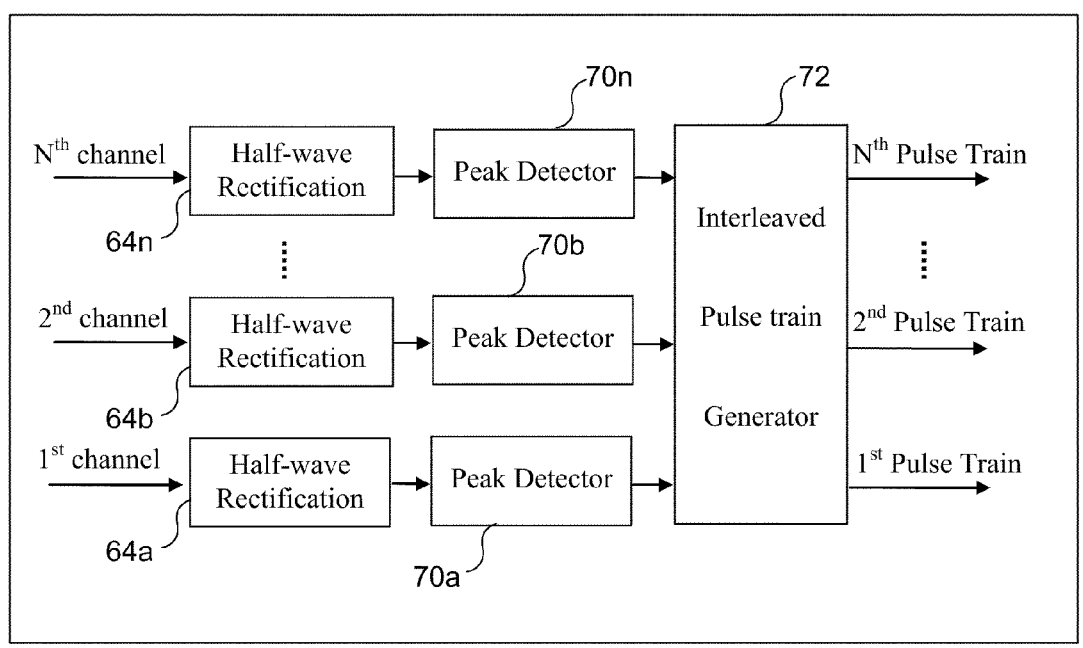

FIG. 3 schematically illustrates coherent fixed carrier demodulation;

FIG. 4A is a functional block diagram of the CIS (Prior Art) cochlear implant signal processing technique;

FIG. 4B is a functional block diagram of an exemplary single-sideband encoder implementing the first exemplary technique of FIG. 2A;

FIG. 5A graphically illustrates exemplary waveforms of sub-band signals of a short segment of music sound;

FIG. 5B graphically illustrates exemplary single sideband demodulated real envelopes obtained using the processing technique of block 22 in FIG. 2A;

FIG. 6 graphically illustrates two exemplary notes of a melody, the Hilbert transform of the two exemplary notes as implemented by prior art signal processing techniques for cochlear implants, and demodulated real envelopes obtained using the processing technique of block 22 in FIG. 2A;

FIGS. 7A and 7C illustrate exemplary pulse train patterns produced by processing two music notes using the CIS (Prior Art) cochlear implant signal processing strategy;

FIGS. 7B and 7D illustrate exemplary pulse train patterns produced by the processing two music notes using the novel first exemplary coherent demodulation technique of FIG. 2A;

FIG. 8 graphically illustrates an exemplary impulse response of a Butterworth low-pass filter;

FIG. 9 graphically illustrates a comparison of melody recognition with acoustic simulations of the CIS (Prior Art) cochlear implant signal processing strategy and the novel first exemplary coherent demodulation technique of FIG. 2A;

FIG. 10 graphically illustrates ratings from cochlear implant patients whose cochlear implants were tested using both the CIS (Prior Art) cochlear implant signal processing strategy and the novel first exemplary coherent demodulation technique of FIG. 2A;

FIG. 11 is a functional block diagram schematically illustrating an exemplary technique for extracting the harmonic components of an audio signal with a series of harmonic separators, to implement the steps corresponding to blocks 30 and 32 in FIG. 2B;

FIG. 12 is a functional block diagram providing exemplary details for implementing the steps corresponding to block 34 in FIG. 2B;

FIG. 13 is a functional block diagram for a first exemplary technique to implement the steps corresponding to block 36 in the novel second exemplary cochlear implant signal processing embodiment shown in FIG. 2B; and FIG. 14 is a functional block diagram for a second exemplary technique to implement the steps corresponding to block 36 in the novel second exemplary cochlear implant signal processing embodiment shown in FIG. 2B.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

Coherent Versus Incoherent Demodulation

Incoherent demodulation utilizes an energetic envelope detector with no phase reference (i.e., no direct knowledge of the carrier). Coherent demodulation explicitly detects well-behaved carriers for modulation filtering, and is better able to maintain signal elements present in the original signal. Significantly, coherent demodulation is more computationally intensive than incoherent demodulation. Because incoherent demodulation is more computationally efficient, and thus, easier to implement for real time signal processing applications, prior art signal processing techniques for cochlear implants have utilized incoherent demodulation.

Figure 1:
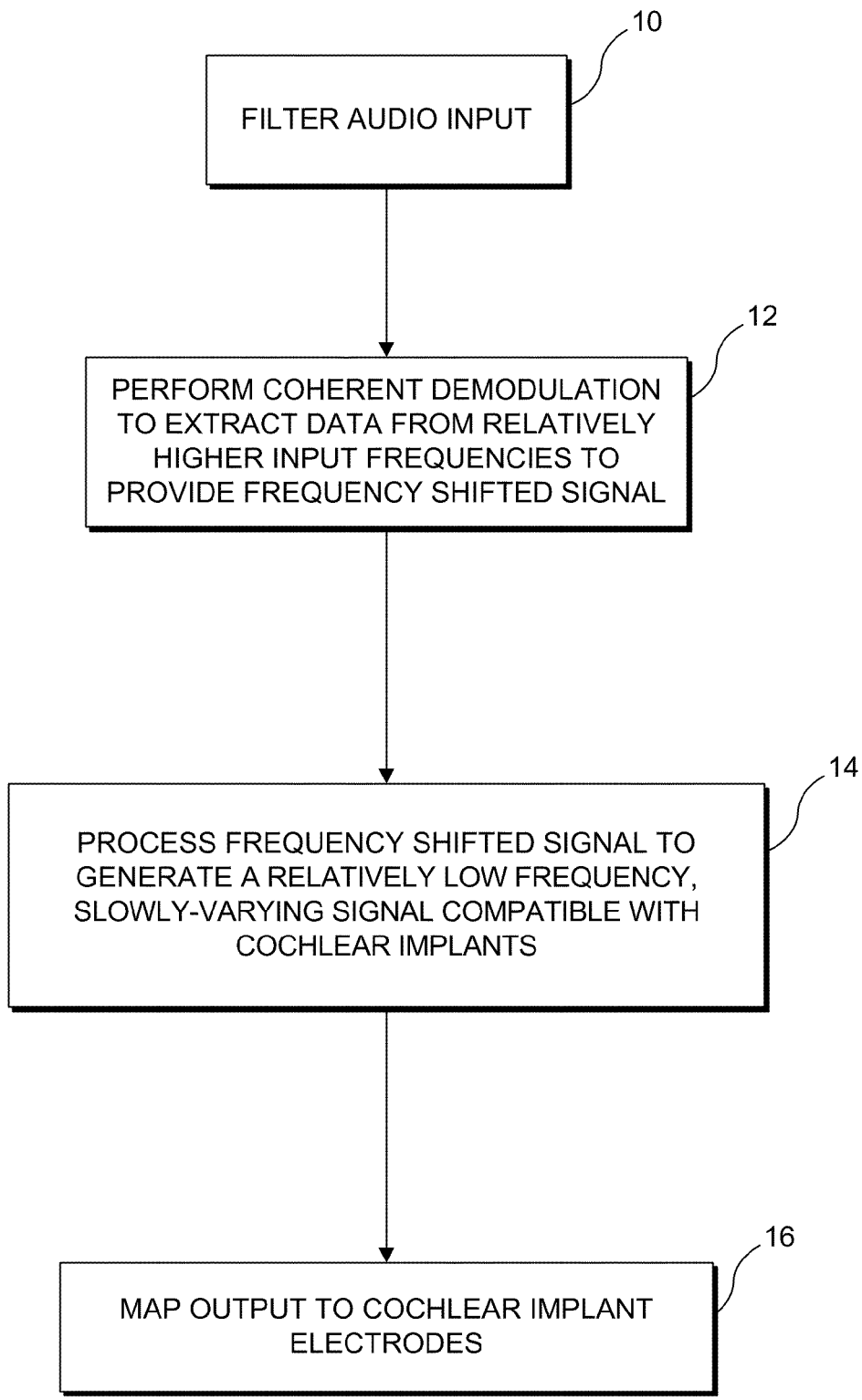

FIG. 1 is a flow chart of exemplary high level method steps for using coherent demodulation in an enhanced signal processing paradigm for use with cochlear implants, which provides enhanced cochlear implant performance by extracting useful information from relatively high frequency portions of an acoustic input (i.e., the temporal fine structure) and including that information in a relatively low frequency, slowly varying signal that is compatible with cochlear implants.

In a block 10, the audio input is filtered. As discussed in detail below, different exemplary embodiments employ different filtering strategies. In a block 12, coherent demodulation filtering is employed to extract useful information from relatively high frequency portions of the audio input to achieve a frequency shifted signal. In a block 14, the frequency shifted signal is processed to include that useful information in a relatively low frequency, slowly varying signal that is compatible with cochlear implants. In a block 16, the slowly varying signal is mapped to electrodes in the cochlear implant.

FIG. 2A is a flow chart showing exemplary method steps that are employed in a first exemplary technique disclosed herein, for using coherent demodulation in an enhanced signal processing paradigm employing bandpass filtering, which is suitable for use with cochlear implants.

FIG. 2B is a flow chart of illustrating exemplary method steps that are used in a second exemplary technique disclosed herein. This second technique employs coherent demodulation in an enhanced signal processing paradigm, which employs harmonic filtering, for use with cochlear implants.

Referring to FIG. 2A, in a block 20, the audio input is filtered using bandpass filtering. In a block 22, coherent demodulation filtering is employed to extracting useful information from relatively high frequency portions of an acoustic input to achieve a frequency shifted signal. In a block 24 the frequency shifted signal is processed, using peak detection or half-wave rectification modulated with a high-rate pulse train, to include that information in a relatively low frequency, slowly varying signal compatible with cochlear implants. In a block 26 the slowly varying signal is mapped to electrodes in the cochlear implant.

Referring to FIG. 2B, in a block 30 the pitch of the audio input is determined. In a block 32 the audio input is separated into a plurality of harmonics as a function of pitch. The number of resulting harmonics should be at least two, although more harmonics can employed. In general, the use of additional harmonics is likely to result in greater performance, although it should be recognized that a specific number of harmonics may work better (or worse) with a specific type of cochlear implant. In a block 34, coherent demodulation is used to shift the frequency of each harmonic downward, to extract useful information from relatively high frequency portions of the acoustic input, producing a frequency shifted signal. Those of ordinary skill in the art will recognize that the input signal likely includes relatively lower frequency portions not relevant to human perception of speech signals or music. Thus, in at least one exemplary embodiment, in addition to separating the input signal into a plurality of harmonics in block 32, the signal processing technique can also employ bandpass filtering to remove such low-frequency content. In other words, in such an embodiment, in block 32 the input signal is separated into portions to be downshifted, and portions to be discarded. However, in at least one further embodiment, the entire input signal is separated into a plurality of harmonics without bandpass filtering to remove such low-frequency content, such that the entire input signal is spectrally shifted downwards.

In a block 36, for each frequency shifted harmonic, amplitude modulation of the pulse train is performed, to include the information from the relatively high frequency portions of the input signal in a relatively low frequency, slowly varying signal compatible with cochlear implants. In a block 38, the slowly varying signal is mapped to electrodes in the cochlear implant.

FIGS. 3-10 relate to the first exemplary cochlear implant signal processing technique of FIG. 2A. Empirical studies based on the first exemplary technique led to modifications to provide even further performance enhancements, resulting in the second exemplary cochlear implant signal processing technique of FIG. 2B. FIGS. 11-14 relate to the second exemplary cochlear implant signal processing technique of FIG. 2B.

First Exemplary Embodiment Using Fixed-Carrier Coherent Demodulation

Referring to block 22 of FIG. 2A, a fixed carrier was utilized to coherently demodulate each sub-band signal as shown in Eq. (5):

$$x(t) = \sum_{k=1}^{N} x_k(t) = \sum_{k=1}^{N} a_k(t) \cdot c_k(t) = \sum_{k=1}^{N} a_k(t) \cdot \cos\omega_k t \quad (5)$$

where $\omega_k$ is a fixed carrier frequency at the lower edge of each sub-band. The envelope $a_k(t)$ is now a real (positive- and negative-going) signal, yet intentionally is not a positive-only Hilbert envelope. This fixed-carrier demodulation is similar to that used in early single sideband receivers; however, the post processing required to generate a usable signal for cochlear implants is significantly different.

FIG. 3 is a functional block diagram illustrating how the fixed carrier demodulation is performed in the first exemplary embodiment of FIG. 2A, wherein "Conj." indicates "conjugate" and "H{.}" represents the Hilbert transform. It is assumed that the fixed carrier resides on the lower edge of the sub-band. Each sub-band was considered to be an upper sideband signal generated from an envelope signal by single sideband modulation. To perform coherent demodulation, an analytic signal was formed for each sub-band by the Hilbert transform. The analytic signal has a one-sided spectrum, and it was then multiplied with a complex carrier at the lower edge of that sub-band, producing a spectrum replica at the base band. The demodulated complex signal was conjugated and summed to construct a real-valued signal.

Note Eqs. 6 and 7 below for each sub-band:

$$g_k(t) = \{x_k(t) + jH[x_k(t)]\} \cdot e^{-j\omega_k t} \quad (6)$$

$$a_k(t) = g_k(t) + g_k^*(t) \quad (7)$$

where the symbol, *, signifies the complex conjugate.

Alternatively, the demodulation can be performed with a product detector, which mixes a sub-band signal with a carrier and then low-passes the mixture.

The coherent envelope signal has a maximum frequency equivalent to its bandwidth. Normally, when a sufficient number of sub-bands is used, the maximum signal bandwidth can be lower than 1000 Hz. Such low bandwidth signals would be within the perceivable range of rate pitch elicited by electrical stimulation in a cochlear implant.

First Exemplary Embodiment of a Coherent Envelope (CE) Encoder

FIG. 4A is a functional block diagram of the CIS (Prior Art) cochlear implant signal processing technique, while FIG. 4B is an exemplary block diagram showing how the exemplary method steps of FIG. 2A are implemented using single-sideband encoding, wherein BPF is an acronym for band-pass filter and CE is an acronym for a coherent envelope demodulator.

A sound signal is first filtered into N bands with equal bandwidth on a logarithmic scale. For instance, exemplary cutoff frequencies are: 300, 462, 687, 996, 1423, 2013, 2827, 3950 and 5500 Hz, when the number of bands is eight. Each band-passed signal is coherently demodulated by single sideband demodulation, as discussed above. FIG. 5A graphically illustrates the waveforms of sub-band signals of an exemplary short segment of music, in response to a 22.7 ms-long melody signal. FIG. 5B graphically illustrates the exemplary music signal after processing using coherent envelopes demodulated with fixed carriers. The bottom trace on each panel corresponds to the lowest frequency sub-band. The coherent envelopes convey both temporal envelope and temporal fine structure cues embedded in each sub-band. It is possible to deliver these analog signals directly to current cochlear implants. One of the advantages of using coherent envelopes is that the demodulated analog signals would significantly reduce channel interactions due to the nature of low rates.

To reduce channel interactions, analog signals should be transformed into interleaved pulse trains in cochlear implants, meaning different stimulating electrodes are sequentially activated within one stimulation cycle.

FIG. 6 graphically illustrates how the coherent demodulation of the input signal disclosed herein differs from the Hilbert transform employed in prior art cochlear implant signal processing techniques. Portion A of FIG. 6 corresponds to two melody notes before processing. Portion B of FIG. 6 corresponds to the Hilbert envelope for the two melody notes, while Portion C of FIG. 6 corresponds to the real coherent envelope of the two melody notes.

For pulsatile stimulation, each analog waveform should be converted into a pulse train. To perform this conversion, pulses are generated in synchrony with the positive peaks in the analog waveforms. The inter-pulse interval then carries zero-crossing cues or phase information. The pulse heights are equal to the amplitudes at the peaks. It has been found that auditory neurons phase lock to temporal peaks only up to 4-5 kHz. Here, a similar mechanism is used for generating pulses.

Finally, these pulses might overlap each other in time. An interleaved pulse train generator is used to detect the overlapping pulses and force them to be interleaved. Within one stimulating cycle, all bands are sequentially scanned to locate a peak. If a peak is found, a flag is raised, indicating that the corresponding electrode should be activated subsequently. A biphasic pulse will be generated to stimulate that electrode and the flag is thereafter cleared. This pulse selection procedure ensures only one pulse at a time is applied during a defined period. Alternatively, stimulating pulses can be generated by sampling the half-wave rectified real coherent envelope with a high-rate pulse train (see FIG. 13 and the related text).

The exemplary processing technique of FIG. 2A (referred to herein as the first CE strategy) has been implemented using a research interface provided by the Cochlear Corporation. This system provides the needed flexibility to generate arbitrary interleaved electrical pulse stimulation patterns, as is required for patients with an implanted cochlear stimulator.

FIGS. 7A and 7C graphically illustrate a pulse train pattern created with the CIS (Prior Art) cochlear implant signal processing technique, and FIGS. 7B and 7D graphically illustrate a pulse train pattern created with the first CE cochlear implant signal processing technique strategy (i.e., the first exemplary embodiment shown in FIG. 2A). All parameters for FIGS. 7A and 7B are identical except that the stimulation rate of the CIS strategy was set at the typically constant 800 pulses per channel, while the parameter for FIGS. 7C and 7D are also the same. The pulse pattern of the first CE strategy intentionally contains detailed temporal cues via time-variable yet independent stimulation rates on each electrode. Electrode 22 of FIGS. 7A and 7B corresponds to a low frequency sub-band.

First Exemplary Embodiment Acoustic Simulations

As a preliminary test of the relative efficacy of the conventional CIS and first proposed CE strategies, acoustic sounds were reconstructed from the above pulse trains. Pulse trains were convolved with the impulse response of a 2nd-order Butterworth low-pass filter at 300 Hz, as shown in FIG. 8, mimicking the deteriorating temporal pitch discrimination ability in electrically-induced hearing. Each filtered signal was modulated by a carrier identical to the demodulation carrier. All signals were summed together to re-synthesize an acoustic sound.

Melody recognition was performed to assess whether the first CE coding strategy could improve music recognition performance. Subjects were asked to identify a closed set of twelve common melodies, e.g. "Happy Birthday," "Frere Jacques," "Jingle Bells," etc. Rhythmic cues were removed, and all 12 melodies were isochronous. During these listening experiments, the subject was allowed to practice twice prior to the test. Each melody was presented twice, and no feedback was given. The stimuli and user interface are part of a battery of tests for assessing cochlear implant users' melody recognition performance.

First Exemplary Embodiment Results

The melody recognition scores from four (4) normal hearing subjects are presented in FIG. 9, which graphically illustrates melody recognition with acoustic simulations of the CIS and SSE strategies (error bars indicate standard errors). The mean score of the SSE is 92%, whereas the mean for CIS is only 57%. A paired-t test suggests that the recognition performance of the SSE strategy is significantly different than that of the CIS strategy.

In a follow up study, the hearing of patients using the Nucleus™ cochlear implant was tested after modifying the cochlear implant to process audio input using the first exemplary cochlear implant signal processing embodiment shown in FIG. 2A. This study indicated improved implant performance using the first exemplary cochlear implant signal processing embodiment; however, the desired melody recognition was not achieved. Additional research lead to the development of the second exemplary cochlear implant signal processing embodiment shown in FIG. 2B. The results of the follow-up study are graphically illustrated in FIG. 10. The rating scores are for sound quality, sound clarity and music perception (1 for the worst, 10 for the best). The test subjects indicated that the CIS coding provided a monotone, with input often being unrecognizable. The test subjects clearly preferred the first exemplary cochlear implant signal processing embodiment shown in FIG. 2A, indicating that they perceived multi-pitch, distinguishable, and pleasant sounds. They did report perceiving some mistuning.

First Exemplary Embodiment Discussion and Conclusions

The SSE strategy presents a faithful representation of a high-frequency signal at the lower rates required for successful cochlear implant electrical stimulation. Higher rates saturate the patient's perception. This signal processing technique can be easily implemented in real-time. Most importantly, it appears that the coherent envelopes provide usable temporal cues to implant users. Since lower-frequency channels normally have sparse pulse trains, implementing interleaved pulse train stimulation is also feasible. The analog version of the SSE strategy provides low-rate analog stimulation comparable to other cochlear implant strategies, with less simultaneous channel interaction.

The fixed-carrier demodulation approach also provides a potentially useful tool for extracting slowly varying features from speech and music.

Second Exemplary Embodiment Using Coherent Demodulation

FIGS. 11-14 and the related descriptive text provide additional details about the second exemplary cochlear implant signal processing embodiment shown in FIG. 2B.

FIG. 11 is a functional block diagram schematically illustrating an exemplary technique for extracting the harmonic components of an audio signal with a series of harmonic separators, to implement the steps corresponding to blocks 30 and 32 in the second exemplary cochlear implant signal processing embodiment shown in FIG. 2B (in which harmonics are extracted from the audio input signal). Referring to FIG. 2B, in block 30, the pitch of the audio input is determined, while in block 32, the audio input is separated into a plurality of harmonics, as a function of pitch.

Referring to FIG. 11, a pre-emphasis filter 50 is first applied to the input audio signal for energy equalization. A pitch tracker 52 is then used to estimate a time-varying fundamental frequency, $F_0(t)$. Based on $F_0(t)$, a harmonic locator 54 splits the audio single into N different harmonics, each different harmonic being output to a harmonic separator (see blocks 56a, 56b, ... 56n). Each harmonic separator is implemented as a bandpass filter specifically customized for that particular harmonic. For example, harmonic separator 56k is implemented as a bandpass filter centered around $K^{th}$ multiples of $F_0(t)$, and its bandwidth is equal to $F_0(t)$. The outputs are a number of selected harmonics, based on the pitch tracker.

It should be noted that the frequency shifting for block 34 (in the second exemplary cochlear implant signal processing embodiment shown in FIG. 2B) can be implemented in at least two different ways (both of which are discussed in detail below). In broad terms, one has the choice of frequency shifting analytic subbands or real-valued subbands. To frequency shift analytic subbands, one first converts a real-valued signal to an analytic signal using the Hilbert transform, and then multiplies the result with a complex carrier. To frequency shift a real-valued signal, one first multiplies the real-valued signal directly with a real-valued carrier, and then performs low-pass filtering. The latter technique does require additional low-pass filtering. Both broad techniques produce the same signal. Note that frequency shifting the analytic subband requires just one filter operation, whereas shifting the real-valued subband requires at least two.

FIG. 12 is a functional block diagram providing exemplary details for implementing the steps corresponding to block 34 in the second exemplary cochlear implant signal processing embodiment shown in FIG. 2B, in which each harmonic is processed such that relatively higher frequency portions of the audio input are frequency shifted downward by manipulating an analytic signal. The information from those relatively higher frequency portions of the audio input are incorporated in the signal generated for controlling the cochlear implant. Referring to FIG. 2B, in a block 34, coherent demodulation is used to shift the frequency of each harmonic downward, to extract useful information from relatively high frequency portions of the acoustic input to achieve a frequency shifted signal.

Referring to FIG. 12, the step of block 34 is implemented using two-sided frequency shifting on selected harmonics output from FIG. 11. For each channel, i.e., each harmonic, the Hilbert transform (see blocks 58a, 58b, 58n) is first applied to obtain a one-sided analytic signal. Note that while the Hilbert transform is employed in prior art cochlear implant signal processing techniques, in the present novel technique, the Hilbert transform is applied to a harmonically separated audio input, whereas in prior art cochlear implant signal processing techniques, the audio input is not separated harmonically, but simply filtered using a bandpass filter. Next, each one-sided analytic harmonic signal is multiplied by a complex exponential signal (as indicated by operators 60a, 60b, ... 60n). The phase term of the complex exponential signal is determined by the fundamental frequency $F_0(t)$, and the targeted temporal pitch trajectory $\hat{F}_0(t)$. Specifically, $\hat{F}_0(t)$ is obtained by linearly (or nonlinearly) mapping $F_0(t)$, $2F_0(t)$, and $NF_0(t)$ to the frequency range of about 50~300 Hz (i.e., the perceivable temporal pitch range of cochlear implant users). $\hat{F}_0(t)$ can be smaller than or equal to $F_0(t)$. The phase term $\phi_k(t)$ of the $K^{th}$ complex exponential function is determined by Eq. (8) as follows:

$$\frac{d\varphi_k(t)}{dt} = g(kF_0(t), \hat{F}_0(t)) \qquad (8)$$

where $g(kF_0(t), \hat{F}_0(t))$ is a linear function.

After multiplying each one-sided analytic harmonic signal with the complex exponential signal, each result is frequency shifted to $\hat{F}_0(t)$ to maintain the harmonic relationship among all channels. Finally, the real part of the complex signal for each harmonic is extracted and output (as indicated by blocks 62a, 62b, ... 62n).

Alternatively, the above two-sided frequency shifting operation can be implemented without using the Hilbert transform. In such an embodiment (frequency shifting a real-valued signal), the processing includes two steps. The first step is to multiply each harmonic with a cosine function $\cos(\phi_k(t))$, whose phase term $\phi_k(t)$ is determined as described above. The second step is to apply a low pass filter to remove double-frequency components.

FIG. 13 is a functional block diagram for a first exemplary technique that can be employed to implement the steps of block 36 in the second exemplary cochlear implant signal processing embodiment shown in FIG. 2B. An amplitude modulation of the pulse train is performed for each frequency shifted harmonic, to include the information from the relatively high frequency portions of the input signal in a relatively low frequency, slowly varying signal that is compatible with cochlear implants.

Referring to FIG. 13, for each channel output from FIG. 12, a half-wave rectifier (see blocks 64a, 64b, . . . 64n) is used to obtain a non-negative envelope signal that carries both amplitude and periodicity information of the frequency-shifted harmonic. A stimulation pulse train is further generated by modulating the envelope signal with a biphasic pulse train at a constant rate (see operators 66a, 66b, . . . 66n). Across all channels, the biphasic pulses are interleaved in time to avoid channel interaction.

It should be noted that harmonic and inharmonic sounds produce noticeably different pulses, which have not been seen in prior art cochlear implant signal processing strategies. In the case of a harmonic input, each amplitude-modulated pulse train is a strong periodic signal with a temporal pitch below 300 Hz. Significantly, the temporal pitch change is within the perceivable range of most cochlear implant users. The periodic signal encodes information about the fundamental frequency ($F_0$) of the harmonic input, which is critical for music perception, voice gender identification, tonal language understanding and speech recognition in noisy environments. In the case of an inharmonic or noise-like input, each pulse train exhibits the properties of an aperiodic signal, which is crucial to consonant recognition and musical instrument identification.

FIG. 14 is a functional block diagram for a second exemplary technique to implement the steps of block 36 in the second exemplary cochlear implant signal processing embodiment shown in FIG. 2B. In this second exemplary technique, a pulse train can be generated with a peak detector, which produces pulses only at the local maxima of the half-wave rectified envelope signal. Pulse sequences are also forced to be interleaved to avoid channel interaction. In this second exemplary technique, the produced pulse trains have variable stimulation rates, rather than a constant rate as discussed with respect to the first exemplary technique of FIG. 13. However, the temporal pattern of variation in each pulse rate encodes either a periodic/harmonic input signal with a regular pulse sequence, or encodes an aperiodic/inharmonic signal with a random/irregular pulse train. This type of pulse train stimulation has been proven effective for cochlear implant patients as well. Note the dashed box indicating that the high-rate pulse trains are interleaved in time.

Referring to FIG. 14, for each channel output from FIG. 12, a half-wave rectifier (see blocks 68a, 68b, . . . 68n) is used to obtain a non-negative envelope signal that carries both amplitude and periodicity information of the frequency-shifted harmonic. In this embodiment, the pulse train is generated using peak detection (see blocks 70a, 70b, . . . 70n), the output of which is interleaved (see block 72).

Referring once again to FIG. 2B, once the pulse train has been produced in block 36, the slowly varying signal is mapped to electrodes in the cochlear implant in block 38. An exemplary mapping technique is described below.

Electrode Assignment

A limited number (N) of harmonics are dynamically tracked according to the $F_0$ contour of the input sound. These harmonics span a wide range of frequency in the spectral domain. However, the actual number of electrodes (M) that can be stimulated varies in a typical patient map. Each electrode corresponds to a specific range of frequency in relation to its tonotopic placement in the cochlea. Typically, the basal electrodes have wider bandwidths centered around higher frequencies, whereas the apical electrodes have narrow bandwidths centered around lower frequencies.

In order to assign N harmonics to M electrodes, the frequency location of the $i^{th}$ harmonic is correlated with the specified frequency range of each individual electrode. The frequency of the $i^{th}$ harmonic is first calculated, and it is then compared with the frequency mapping of a cochlear implant patient. If the $i^{th}$ harmonic falls in the spectral coverage of one electrode, the $i^{th}$ amplitude-modulated pulse train is assigned to this corresponding electrode. When two or more harmonics compete for the same electrode, those pulse trains are summed together to produce a single stimulation signal.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for processing an audio input to generate a signal for controlling a cochlear implant for a hearing impaired patient, the method comprising the steps of:
   (a) providing an auditory input signal;
   (b) performing a coherent demodulation of the auditory input signal to generate a frequency shifted signal, using a targeted temporal pitch trajectory comprising a frequency range of about 50 Hz to about 300 Hz;
   (c) processing the frequency shifted signal to generate a relatively low frequency, slowly varying signal that is compatible with the cochlear implant; and
   (d) mapping the relatively low frequency, slowly varying signal to at least one of a plurality of cochlear implant stimulation electrodes.

2. The method of claim 1, wherein before the step of performing coherent demodulation of the auditory input signal, further comprising the step of separating the auditory input signal into a plurality of sub bands using a plurality of bandpass filters.

3. The method of claim 2, wherein the step of performing the coherent demodulation of the auditory input signal comprises the steps of:
   (a) for each sub band, assuming a carrier portion of the auditory input signal is fixed at a lower boundary of the sub band; and
   (b) extracting a coherent envelope for each sub band, each coherent envelope comprising a spectrally shifted real value signal, the frequency shifted signal corresponding to a sum of spectrally shifted real value signals for the plurality of sub bands.

4. The method of claim 1, wherein before the step of performing coherent demodulation of the auditory input signal, further comprising the steps of:

(a) determining a pitch of the auditory input signal over time; and
(b) separating the auditory input signal into a plurality of different harmonics over time as a function of the pitch of the auditory input signal over time.

5. The method of claim 4, wherein the step of performing coherent demodulation of the auditory input signal to generate a frequency shifted signal comprises the step of extracting a coherent envelope for each different harmonic, each coherent envelope comprising a spectrally shifted real value signal, the frequency shifted signal corresponding to a sum of spectrally shifted real value signals for the plurality of harmonics.

6. The method of claim 4, wherein the step of performing coherent demodulation of the auditory input signal to generate a frequency shifted signal comprises the steps of:
 (a) performing a Hilbert transform on each harmonic, thereby generating a one-sided analytic signal for each harmonic;
 (b) multiplying each one-sided analytic signal by a complex exponential signal, a phase term of the complex exponential signal being a function of a fundamental frequency of the auditory input signal and the targeted temporal pitch trajectory, thereby generating a frequency shifted complex signal for each harmonic; and
 (c) isolating a real part of the frequency shifted complex signal for each harmonic, the frequency shifted signal corresponding to a sum of each real part of the frequency shifted complex signal for each harmonic.

7. The method of claim 4, wherein the step of performing coherent demodulation of the auditory input signal to generate a frequency shifted signal comprises the steps of:
 (a) multiplying each harmonic by a cosine function having a phase term that is a function of a fundamental frequency of the auditory input signal and a targeted temporal pitch trajectory, thereby generating a frequency shifted harmonic signal for each harmonic; and
 (b) applying a low pass filter to each frequency shifted harmonic signal to remove double-frequency components, the frequency shifted signal corresponding to a sum of filtered frequency shifted harmonic signals.

8. The method of claim 7, wherein the targeted temporal pitch trajectory comprises a frequency range of about 50 Hz to about 300 Hz.

9. The method of claim 1, wherein the step of processing the frequency shifted signal to generate a relatively low frequency, slowly varying signal compatible with the cochlear implant comprises the steps of:
 (a) passing the frequency shifted signal through a half-wave rectifier to obtain a non-negative envelope signal that carries both amplitude and periodicity information of the frequency shifted signal; and
 (b) modulating the non-negative envelope signal with a biphasic pulse train at a constant rate to generate the relatively low frequency, slowly varying signal that is compatible with the cochlear implant.

10. The method of claim 1, wherein the step of processing the frequency shifted signal to generate a relatively low frequency, slowly varying signal compatible with the cochlear implant comprises the steps of:
 (a) passing the frequency shifted signal through a half-wave rectifier to obtain a non-negative envelope signal that carries both amplitude and periodicity information of the frequency shifted signal;
 (b) performing peak detection on the non-negative envelope signal to obtain a peak envelope signal; and
 (c) processing the peak envelope signal to generate the relatively low frequency, slowly varying signal compatible with the cochlear implant.

11. A method for controlling a cochlear implant for a hearing impaired patient, the method comprising the steps of:
 (a) providing an auditory input signal;
 (b) determining a pitch of the auditory input signal over time;
 (c) separating the auditory input signal into a plurality of harmonics over time as a function of the pitch over time;
 (d) for each of the plurality of harmonics, shifting the frequency of the harmonic downward, generating a plurality of frequency shifted harmonics;
 (e) for each frequency shifted harmonic, performing an amplitude modulation, generating a plurality of frequency shifted and amplitude modulated harmonics; and
 (f) mapping each frequency shifted and amplitude modulated harmonic to different ones of a plurality of cochlear implant stimulation electrodes.

12. The method of claim 11, wherein the step of shifting the frequency of the harmonic downward for each harmonic comprises the step of performing a coherent demodulation of each harmonic to obtain the plurality of frequency shifted harmonics.

13. The method of claim 12, wherein the step of performing the coherent demodulation of each harmonic to obtain the plurality of frequency shifted harmonics comprises the steps of:
 (a) performing a Hilbert transform on each harmonic, thereby generating a one-sided analytic signal for each harmonic;
 (b) multiplying each one-sided analytic signal by a complex exponential signal, a phase term of the complex exponential signal being a function of a fundamental frequency of the auditory input signal and a targeted temporal pitch trajectory, thereby generating a frequency shifted complex signal for each harmonic; and
 (c) isolating a real part of the frequency shifted complex signal for each harmonic, the frequency shifted signal corresponding to a sum of real parts of the frequency shifted complex signal for each harmonic.

14. The method of claim 13, wherein the targeted temporal pitch trajectory comprises a frequency range of about 50 to about 300 Hz.

15. The method of claim 12, wherein the step of performing the coherent demodulation of each harmonic to obtain the plurality of frequency shifted harmonics comprises the steps of:
 (a) multiplying each harmonic by a cosine function whose phase term is a function of a fundamental frequency of the auditory input signal and a targeted temporal pitch trajectory, thereby generating a frequency shifted harmonic signal for each harmonic; and
 (b) applying a low pass filter to each frequency shifted harmonic signal to remove double-frequency components, the frequency shifted signal corresponding to a sum of the frequency shifted harmonic signals.

16. The method of claim 11, wherein the step of performing an amplitude modulation for each frequency shifted harmonic comprises the steps of:
 (a) passing each frequency shifted harmonic through a half-wave rectifier to obtain a non-negative envelope signal that carries both amplitude and periodicity information of the frequency shifted harmonic; and (b) modulating each non-negative envelope signal with a biphasic pulse train at a constant rate to generate the plurality of frequency shifted and amplitude modulated harmonics.

17. The method of claim 11, wherein the step of performing an amplitude modulation for each frequency shifted harmonic comprises the steps of:
   (a) passing the frequency shifted signal through a half-wave rectifier to obtain a non-negative envelope signal that carries both amplitude and periodicity information of the frequency shifted signal;
   (b) performing peak detection on each non-negative envelope signal to obtain a plurality of peak envelope signals; and
   (c) processing each peak envelope signal to generate the plurality of frequency shifted and amplitude modulated harmonics.

18. A cochlear implant for a hearing impaired patient, comprising:
   (a) at least one acoustic sensor for providing an auditory input signal;
   (b) a power supply;
   (c) a plurality of stimulation electrodes; and
   (d) a processor for controlling the plurality of stimulation electrodes based on the auditory input signal, the processor implementing the functions of:
      (i) performing a coherent demodulation of the auditory input signal to generate a frequency shifted signal, using a targeted temporal pitch trajectory comprising a frequency range of about 50 Hz to about 300 Hz;
      (ii) processing the frequency shifted signal to generate a relatively low frequency, slowly varying signal that is compatible with the cochlear implant; and
      (iii) mapping the relatively low frequency, slowly varying signal to at least one of the plurality of stimulation electrodes.

19. The cochlear implant of claim 18, wherein the processor further implements the functions of:
   (a) determining a pitch of the auditory input signal over time; and
   (b) separating the auditory input signal into a plurality of different harmonics over time as a function of the pitch over time.

20. The cochlear implant of claim 19, wherein the processor generates the frequency shifted signal by implementing the functions of:
   (a) performing a Hilbert transform on each harmonic, thereby generating a one-sided analytic signal for each harmonic;
   (b) multiplying each one-sided analytic signal by a complex exponential signal, a phase term of the complex exponential signal being a function of a fundamental frequency of the auditory input signal and the targeted temporal pitch trajectory, thereby generating a frequency shifted complex signal for each harmonic; and
   (c) isolating a real part of the frequency shifted complex signal for each harmonic, the frequency shifted signal corresponding to a sum of real parts of the frequency shifted complex signal for each harmonic.

21. The cochlear implant of claim 19, wherein the processor generates the frequency shifted signal by implementing the functions of:
   (a) multiplying each harmonic by a cosine function having a phase term that is a function of a fundamental frequency of the auditory input signal and a targeted temporal pitch trajectory; thereby generating a frequency shifted harmonic signal for each harmonic; and
   (b) applying a low pass filter to each frequency shifted harmonic signal to remove double-frequency components, the frequency shifted signal corresponding to a sum of frequency shifted harmonic signals.

22. The cochlear implant of claim 18, wherein the processor manipulates the frequency shifted signal to generate the relatively low frequency, slowly varying signal that is compatible with the cochlear implant frequency shifted signal by implementing the functions of:
   (a) passing the frequency shifted signal through a half-wave rectifier to obtain a non-negative envelope signal that carries both amplitude and periodicity information of the frequency shifted signal; and
   (b) modulating the non-negative envelope signal with a biphasic pulse train at a constant rate to generate the relatively low frequency, slowly varying signal compatible with the cochlear implant.

23. The cochlear implant of claim 18, wherein the processor manipulates the frequency shifted signal to generate the relatively low frequency, slowly varying signal compatible with the cochlear implant frequency shifted signal by implementing the functions of:
   (a) passing the frequency shifted signal through a half-wave rectifier to obtain a non-negative envelope signal that carries both amplitude and periodicity information of the frequency shifted signal;
   (b) performing peak detection on the non-negative envelope signal to obtain a peak envelope signal; and
   (c) processing the peak envelope signal to generate the relatively low frequency, slowly varying signal that is compatible with the cochlear implant.

24. A cochlear implant for a hearing impaired patient, comprising:
   (a) at least one acoustic sensor for providing an auditory input signal;
   (b) a power supply;
   (c) a plurality of stimulation electrodes; and
   (d) a processor for controlling the plurality of stimulation electrodes based on the auditory input signal, the processor implementing the functions of:
      (i) determining a pitch of the auditory input signal over time;
      (ii) separating the auditory input signal into a plurality of harmonics over time as a function of the pitch over time;
      (iii) for each of the plurality of harmonics, shifting the frequency of the harmonic downward, generating a plurality of frequency shifted harmonics;
      (iv) for each frequency shifted harmonic, performing an amplitude modulation, generating a plurality of frequency shifted and amplitude modulated harmonics; and
      (v) mapping each frequency shifted and amplitude modulated harmonic to at least one of a plurality of stimulation electrodes.

* * * * *